United States Patent [19]

Okahata et al.

[11] Patent Number: 4,548,955
[45] Date of Patent: Oct. 22, 1985

[54] NYLON CAPSULE RESPONDING TO PH

[75] Inventors: Yoshio Okahata, Kanagawa; Tokahiro Seki, Tokyo, both of Japan

[73] Assignee: Sogo Pharmaceutical Company Limited, Tokyo, Japan

[21] Appl. No.: 704,884

[22] Filed: Feb. 25, 1985

[51] Int. Cl.⁴ .............................................. C08J 9/36
[52] U.S. Cl. ...................................... 521/53; 424/78; 521/55
[58] Field of Search ....................... 424/78; 521/53, 55

[56] References Cited

U.S. PATENT DOCUMENTS 4,266,030 5/1981 Tschang et al. ...................... 521/53
4,339,500 7/1982 Yanagihara et al. .................. 521/53

Primary Examiner—Morton Foelak
Attorney, Agent, or Firm—Browdy and Neimark

[57] ABSTRACT

The present invention relates to a nylon capsule to whose pore portion is applied a bimolecular membrane so that the capsule can respond to pH.

The nylon capsule accommodates various matters such that they can be released into the outside depending on the change of pH. The nylon capsule is useful, for example, for the missile treatment of anticancer drugs, and as a gradually-releasing microcapsule.

1 Claim, 3 Drawing Figures

NYLON CAPSULE RESPONDING TO PH

DETAILED DESCRIPTION OF THE INVENTION

The present invention relates to a nylon capsule and more particularly to a nylon capsule having a quite new structure in which the membrane permeability is reversibly changed according to the delicate change of pH.

Vesicle having a membrane which can reversibly change its permeability in response to outer stimulations such as change in outer pH is a useful substance for studies and practical use as the reaction model in a living body and carrier of medicines in wide fields of medical treatment, diagnosis and physiological metabolism. It is then said that the vesicle is a kind of artificial cell. Furthermore, the vesicle can be effectively used as a pH indicator if the membrane is adapted to open and close in response to the change of pH so that a colored liquid or the like previously stored in the vesicle flows out. It can be effectively used as a tool for measurement and analysis in the fields of science and engineering, biology, and medical science. Consequently, the new development of such a substance has been strongly wanted in the industry.

The present invention was made in view of the existing state of the art. It was made for the purpose of producing a vesicle or capsule showing an unknown excellent response to pH in commercial quantity by the art of man without using biomatters.

Synthetic high molecular substances were thought to be suitable for the base material in respects of price, stable quality and easy treatment. The inventors examined a large number of synthetic high molecular substances in all aspects and reached the selection of nylon out of the synthetic high molecular substances. In view of the usual plastic art, such is the state that nylon of high porosity and high hygroscopicity is not welcomed. In the present invention, however, porous nylon is suitable for the base material. Therefore, it can be said that the invention found a new use for nylon of inferior quality.

Figure 1:
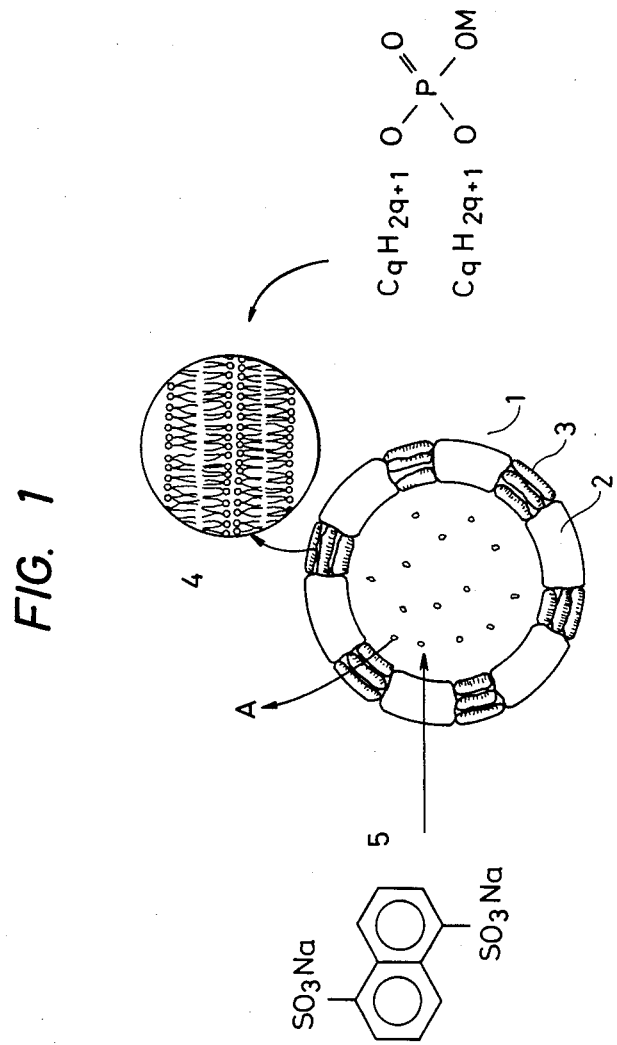
FIG. 1 is a sectional view of the nylon capsule of the invention, partly enlarged to show the scheme of the capsule.
Figure 2:
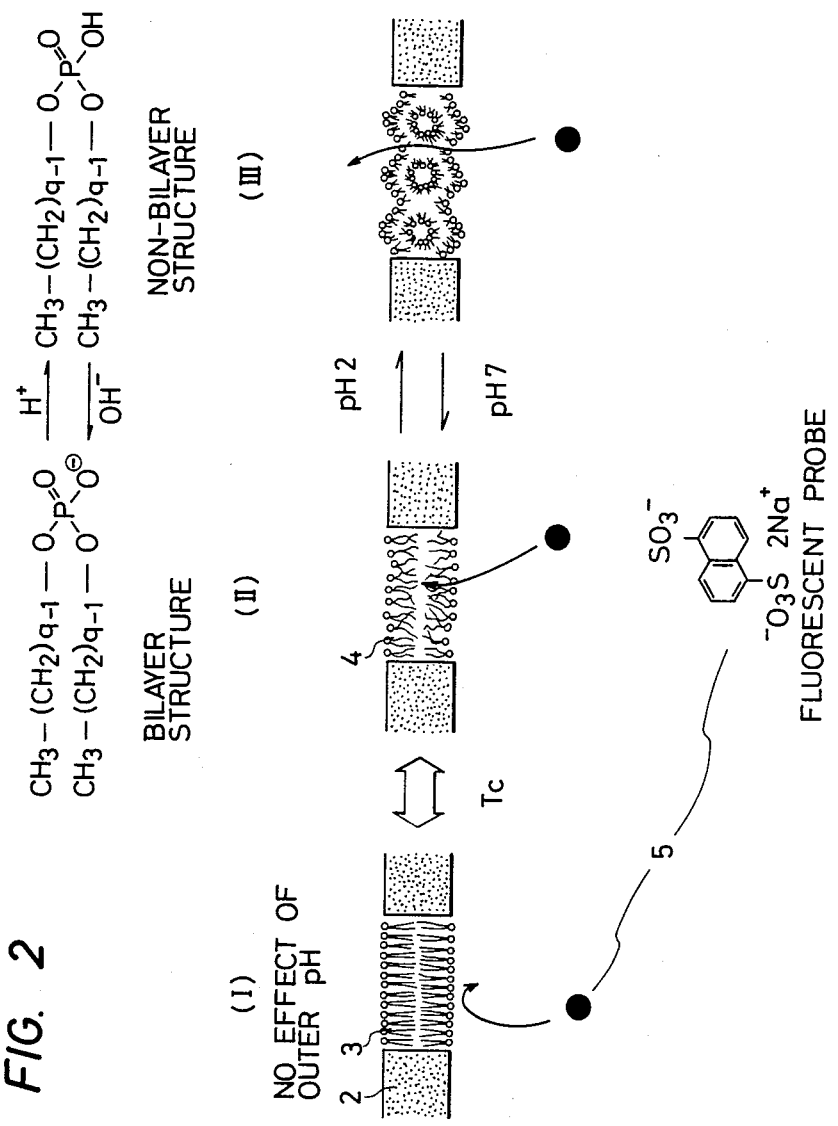
FIG. 2 is a scheme illustrating the mechanism of the membrane permeability of the nylon capsule.

1—nylon capsule
4—bimolecular membrane
5—fluorescent probe
(a)—capsule uncoated with bimolecular membrane (56° C.)
(b)—capsule coated with bimolecular membrane (56° C., above $T_c$)
(c)—capsule coated with bimolecular membrane (25° C., below $T_c$)

After the preparation, the nylon capsule was dialyzed in a phosphoric acid buffer containing 1,5-naphthalenedisulfonic acid disodium salt as a fluorescent probe to trap the fluorescent probe in the hollow portion of the capsule. The resulting nylon capsule was then placed in a dodecane solution of sodium didodecylphosphate. As a result, it was found that the dialkyl compound is applied to the pore portion of the nylon capsule and has a bilayer structure. Hereafter, the nylon capsule was placed in water (pH 2). As a result, the fluorescent probe trapped in the capsule unexpectedly permeated towards the outside of the capsule. The permeation of the fluorescent probe ceased when the water was adjusted to pH 7. The quite new information that the reaction is reversible was obtained.

Namely, according to the new information obtained, the above dialkyl compound becomes a compound forming a bimolecular membrane. Consequently, a nylon membrane comprised of the dialkyl compound applied to the pore portion becomes a kind of cell membrane. It is then said that the capsule having such a nylon membrane is a kind of artificial cell having ion gates which open and close in response to the change of pH.

Further, after the preparation of the capsule from nylon, a saline solution was included in the capsule. The capsule was then placed in a dodecane solution of dialkyl compound ($2C_{12}$-suc-COO$^\ominus$) of the formula

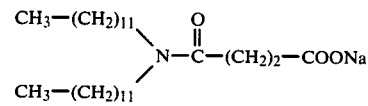

As a result, it was found that the dialkyl compound is applied to the pore portion of the nylon capsule and has a bilayer structure. Hereafter, the nylon capsule was placed in water (pH 2). As a result, the salt placed in the capsule unexpectedly permeated towards the outside of the capsule. The permeation of the salt ceased when the water was adjusted to pH 7. The quite new information that the reaction is reversible was obtained.

Namely, according to the new information obtained, the above dialkyl compound becomes a compound forming a bimolecular structure. Consequently, a nylon membrane comprised of the dialkyl compound applied to the pore portion becomes a kind of cell membrane. It is then said that the capsule having such a nylon membrane is a kind of artificial cell having ion gates which open and close in response to the change of pH.

Based on the new informations obtained, the inventors carried out extensive and intensive studies of nylon as the base of the capsule, screening of bimolecular membrane-forming compounds other than the above dialkyl compound and other investigations, and finally came to the completion of the invention.

That is to say, the present invention relates to a nylon capsule surrounded by a nylon membrane comprised of a particular bimolecular membrane-forming compound applied to the pore portion of the capsule with nylon as the base.

The nylon capsule is made by the ordinary method, namely, by carrying out the reaction of diamine with dibasic acid, or by polymerizing or polycondensing amino acid or lactam. 6,6-nylon, 6,10-nylon, 2,12-nylon and others may be used according to circumstances. For example, the nylon capsule is made by proper methods such as interfacial polymerization method which comprises dissolving acid chloride of dibasic acid in an organic solvent unmiscible with water, adding alkali solution of diamine to the solvent, and instantaneously forming the nylon capsule in the interface between the two liquid phases. The size of the capsule can be regulated at liberty by such a method that the volume of a drop of the diamine alkali solution is changed.

According to the invention, the nylon capsule is dialyzed in a buffer solution of matters to be trapped to admit the matters to the hollow portion of the capsule. The nylon capsule is then admitted into and allowed to stand in a solution of bimolecular membrane-forming compound dissolved in an organic solvent to obtain the desired nylon capsule to whose pore portion is applied the bimolecular membrane-forming compound.

In the nylon capsule thus obtained, the structure of the bimolecular membrane-forming compound applied to the pore portion is destroyed by the change of outer pH at the prescribed temperature, and the matters in the capsule permeates towards the outside. The further change of the outer pH restores the structure of the bimolecular membrane-forming compound to the original state to stop or lower the permeation of the matters. It is then said that the nylon capsule of the invention is a kind of vesicle, that is, a capsule surrounded by a nylon membrane having a large number of ion gates which open and close in response to the change of pH. The structure shows a striking resemblance to that of the cell in a living body. Although the mechanism of the opening and closing of the ion gate remains to be proved, it is possible to take the following view. When the bimolecular membrane is in a state of gel, the charge on the bimolecular membrane-forming compound does not change even if outer pH is changed. Consequently, though the membrane is high in barrier ability, at temperatures above liquid crystal phase transition temperature ($T_c$), the membrane-forming compound is readily protonated to destroy the bilayer structure when the pH of outer water phase is 2. Thus, the membrane permeability is rapidly enhanced, allowing the matters in the hollow portion of the capsule to go out into the outer water phase, which show the prescribed actions, respectively. When the outer water phase is adjusted to, for example, pH 7, the membrane reversibly returns to the original bilayer structure and becomes a membrane high in barrier ability, stopping the permeation of the matters from the nylon capsule. Taking the above-described anionic bimolecular membrane-forming compound represented by $2C_{12}$-suc-COO$^\ominus$ as an example, the relations are estimated to be explained as follows.

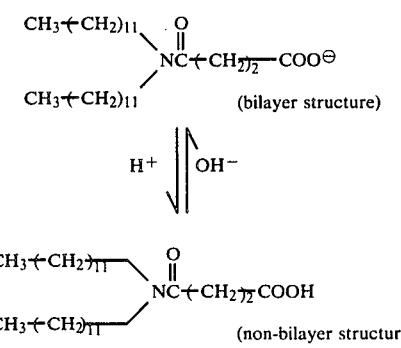

Examples of the compound forming a bimolecular membrane include:

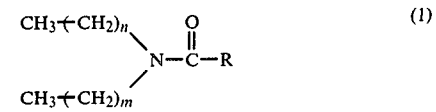

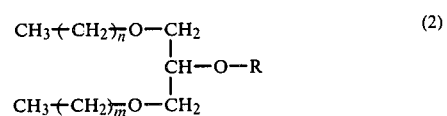

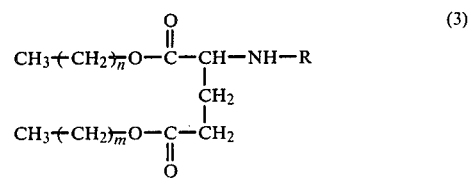

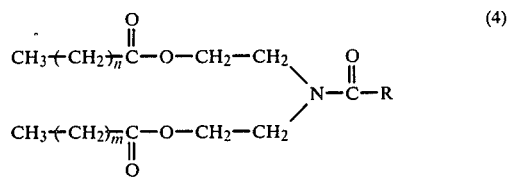

in which n and m independently represent an integer of 9 through 19, and R is a member selected from the following groups:

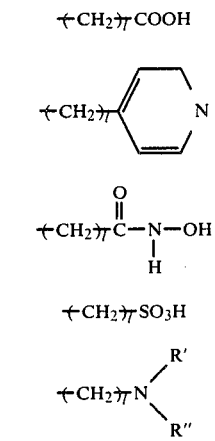

wherein l is an integer of 1 through 5, and R' and R'' independently represent H or CH$_3$.

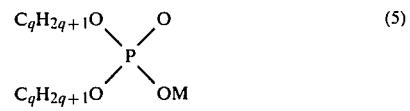

in which q is an integer of 7 through 20, and M represents a metallic atom.

Among the compounds, metallic salts, such as sodium salt and potassium salt, of higher dialkyl phosphoric acid having 7 to 20 carbon atoms can be used advantageously. For example, appropriate compounds include sodium salts or potassium salts of didodecyl phosphoric acid, diheptyl phosphoric acid, dinonyl phosphoric acid, diundodecyl phosphoric acid, ditridecyl phosphoric acid, dinonadecyl phosphoric acid, dieicosanyl phosphoric acid, etc. Needless to say, dialkyl compounds having 8 to 17 carbon atoms can be used advantageously.

As has been described in detail, the nylon capsule of the invention is made through processes, namely, preparation of a nylon capsule, enclosure of matters in the capsule, and application of a compound forming a bimolecular membrane to the pore portion of the nylon capsule. Since the processes themselves do not require a great deal of skill, the nylon capsule is very favorable for the mass production on a commercial basis.

In addition, the membrane permeability is delicately and reversibly changed in response to the change of pH, and the nylon capsule has a long life. Accordingly, the nylon capsule can be used for various purposes over a long period of time.

In the nylon capsule surrounded by the nylon membrane comprised of a bimolecular membrane-forming compound, various matters are easily trapped in the capsule depending on purposes. The capsule of the invention can be used for various purposes. For example, it is widely used for the measurements of membrane permeability using a saline solution and fluorescent probe represented by the formula shown below; missile treatments of anticancer drugs and other medicines, and gradually-releasing microcapsule; fermentation using enzymes or microorganisms; production of antibodies and other immune matters using antigens; and various physiological models using tissues, and industrial, biological, medical, agriculture chemical and pharmaceutical purposes.

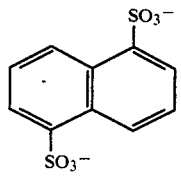

The present invention is described more in detail by way of specific examples of the practice and measurement examples.

EXAMPLE 1

1 m mol of 1,10-bis(chlorcarbonyl)decane and 0.03-0.1 m mol of trymesoil chloride as a cross linking agent were dissolved in 100 ml of mixed solvent, and 80 ml of the resulting solution was placed in a Petri dish (diameter: 15 cm). 2 ml of aqueous solution containing ethylene diamine and (0.38M) and NaOH (0.8M) was added dropwise to the acid chlorido solution using a glass cylinder with a No. 1 stainless needle. During this process, the Petri dish was being vibrated greatly. After the dropping, residual acid chloride solution (20 ml) was added, and the reaction was carried out for 10 minutes with shaking of the Petri dish. After the completion of the reaction, the resulting solution was decantated, and capsules were washed with mixed organic solvent for three times. By this method, nylon capsules (diameter: 2-2.5 mm, membrane thickness: 5-10 μm) of the uniform particle size were obtained.

EXAMPLE 2

The nylon capsules made in Example 1 were fully dialyzed in 0.1M of saline solution for 3 days to trap the saline solution in the hollow portions of the capsules.

After taking out 10 nylon capsules in whose hollow portions are enclosed saline solution, they were placed in a solution prepared by dissolving 10 mg of dialkyl compound of the formula

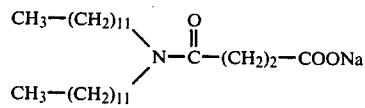

in 1 ml of dodecane with heating to 60° C. Hereafter, they were cooled to room temperature, and then permitted to stand for 1 hour to obtain the desired nylon capsules.

EXAMPLE 3

Using the nylon capsule (diameter: 2 mm, membrane thickness: 1 μm) made in Example 1, it was dialyzed in 0.01M phosphoric acid buffer containing $1 \times 10^{-3}$M of fluorescent probe of the formula

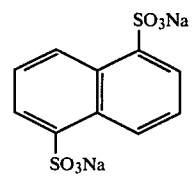

to enclose the fluorescent probe in the hollow portion of the capsule. The resulting capsule was placed in a dodecane solution of bimolecular membrane-forming compound of the formula

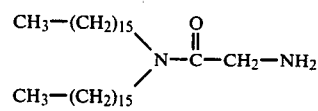

to obtain the desired nylon capsule.

EXAMPLE 4

The procedure of Example 3 was followed but using the dialkyl compound (2C$_{12}$-suc-COO$^\ominus$) employed in Example 2 to obtain the desired fluorescent probe-containing nylon capsules responding to pH.

EXAMPLE 5

The procedure of Example 2 was followed but using the compounds shown below instead of the dialkyl compound to obtain the desired saline solution-containing nylon capsules coated with bimolecular membranes.

The nylon capsules thus obtained were found to be very excellent in reversible response to pH as a result of measurements performed in accordance with the measurement examples (described later).

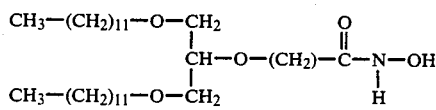

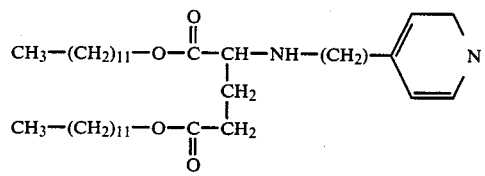

-continued

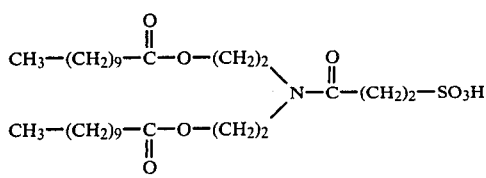

MEASUREMENT EXAMPLE 1

The nylon capsules made in Example 4 were placed in quartz cells. Using 0.1N HCl and 0.1N NaOH, the outer water phases were changed to pH 2 and pH 7. The changes in fluorescent strength with the lapse of time were measured by fluorescent spectroscopy, and the results as shown in FIG. 3 were obtained.

Figure 3:
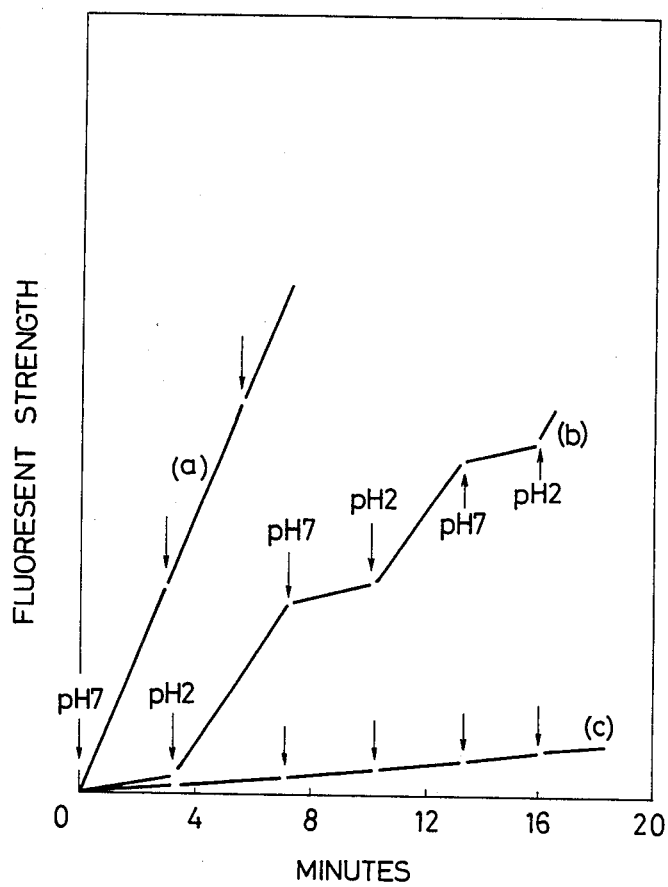
FIG. 3 is a diagram illustrating the changes in the permeability of a fluorescent probe in Measurement Example 1.

FIG. 3 illustrates reversible changes of the permeability of the fluorescent probe from the nylon capsules. The figure shows the changes in fluorescent strength of water phases outside the capsules with the lapse of time when the outer pH is changed to 2 and 7. In the capsules uncoated with bimolecular membranes, the permeation took place rapidly, and the membrane permeability of the probe was not changed by outer pH changes. In the capsules coated with bimolecular membranes ($2C_{12}$-suc-COO$^\ominus$), the permeation took place slowly at a low temperature of 25° C., that is, at temperatures below $T_c$, and almost no difference was recognized in membrane permeability even if the outer pH was changed to 2 and 7. At a high temperature of 56° C., however, the probe hardly permeated when the outer pH was 7, but the membrane permeability was enhanced by 9 to 10 times when the outer pH was changed to 2. The membrane permeability returned to the original state when the outer pH was returned to neutrality. It was possible to repeat such a change of membrane permeability for several times without causing damage to the bimolecular membrane and capsule membrane.

MEASUREMENT EXAMPLE 2

The nylon capsule made in Example 2 was placed in a cell. A slight amount of aqueous solution of 0.1M HCl was added to the outer water phase. Changing the pH of the outer water phase to 2, the membrane permeability from the inner water phase of the capsule to the outer water phase was followed by the measurement of electric conductivity.

As a result, it was proved that NaCl permeates towards the outside of the capsule when the pH of the outer water phase becomes 2.

EXAMPLE 6

Nylon capsules were made by the ordinary method. Namely, 1 m mol of 1,10-bis(chlorcarbonyl)decane and 0.03-0.1 m mol of trymesoil chloride as a cross linking agent were dissolved in 100 ml of mixed solvent, and 80 ml of the resulting solution was placed in a Petri dish (diameter: 15 cm). 2 ml of aqueous solution containing ethylene diamine (0.38M) and NaOH (0.8M) was added dropwise to the acid chloride solution using a glass cylinder with a No. 1 stainless needle. During this process, the Petri dish was being vibrated gently. After the dropping, residual acid chlorido solution (20 ml) was added, and the reaction was carried out for 10 minutes with shaking of the Petri dish. After the completion of the reaction, the resulting solution was decantated, and capsules were washed with mixed organic solvent for three times. By this method, nylon capsules (diameter: 2-2.5 mm, membrane thickness: 1-10 μm) of the uniform particle size were obtained.

After collecting the nylon capsules (diameter: 2 mm, membrane thickness: 1 μm), they were dialyzed in 0.01M phosphoric acid buffer containing $1 \times 10^{-3}$M of fluorescent probe of the formula

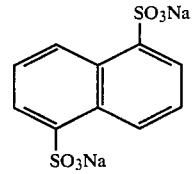

by the ordinary method to enclose the fluorescent probe in the hollow portions of the capsules.

The resulting capsules were placed in a solution prepared by dissolving 10 mg of amphipatic bimolecular membrane-forming compound comprised of didodecyl phosphoric acid sodium salt of the formula

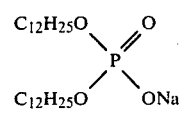

in 1 ml of dodecane with heating to 60° C. Hereafter, they were cooled to room temperature, and then permitted to stand for 1 hour to obtain the desired nylon capsules.

EXAMPLE 7

1 m mol of 1,10-bis(chlorcarbonyl)decane and 0.03-0.1 m mol of trymesoil chloride as a cross linking agent were dissolved in 100 ml of mixed solvent, and 80 ml of the resulting solution was placed in a Petri dish (diameter: 15 cm). 2 ml of aqueous solution containing ethylene diamine (0.38M) and NaOH (0.8M) was added dropwise to the acid chlorido solution using a glass cylinder with a No. 1 stainless needle. During this process, the Petri dish was being vibrated gently. After the dropping, residual acid chlorido solution (20 ml) was added, and the reaction was carried out for 10 minutes with shaking of the Petri dish. After the completion of the reaction, the resulting solution was decantated, and capsules were washed with mixed organic solvent for three times. By this method, nylon capsules (diameter: 2-2.5 mm, membrane thickness: 5-10 μm) of the uniform particle size were obtained.

EXAMPLE 8

The nylon capsules made in Example 7 were fully dialyzed in 0.1M of saline solution for 3 days to trap the saline solution in the hollow portions of the capsules.

After taking out 10 nylon capsules in whose hollow portions are enclosed saline solution, they were placed in a solution prepared by dissolving 10 mg of dialkyl compound of the formula

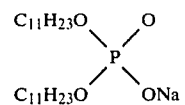

in 1 ml of dodecane with heating to 60° C. Hereafter, they were cooled to room temperature, and then permitted to stand for 1 hour to obtain the desired nylon capsules.

EXAMPLE 9

Using the nylon capsule (diameter: 2 mm, membrane thickness: 1 μm) made in Example 7, it was dialyzed in 0.01M phosphoric acid buffer containing $1\times10^{-3}$M of fluorescent probe of the formula

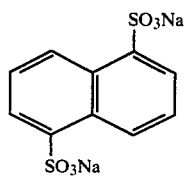

to enclose the fluorescent probe in the hollow portion of the capsule. The resulting capsule was placed in a dodecane solution of bimolecular membrane-forming compound of the formula

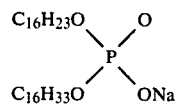

to obtain the desired nylon capsule.

EXAMPLE 10

The procedure of Example 3 was followed but using sodium ditridecylphosphate as a bimolecular membrane-forming compound to obtain the desired fluorescent probe-containing nylon capsules responding to pH.

EXAMPLE 11

The procedure of Example 8 was followed but using the compounds shown below instead of the dialkyl compound to obtain the desired saline solution-containing nylon capsules coated with bimolecular membranes.

The nylon capsules thus obtained were found to be very excellent in reversible response to pH by examining electric conductivity changes with salt permeation.

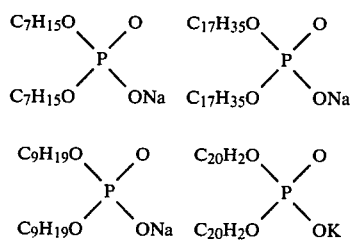

-continued

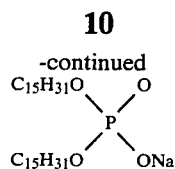

What is claimed is:

1. A nylon capsule responding to pH, wherein one or more compounds selected from the group consisting of compounds represented by the following formulas (1)–(5) are applied to the pore portion:

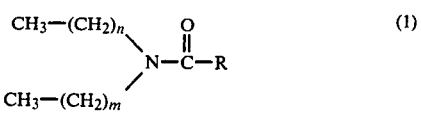

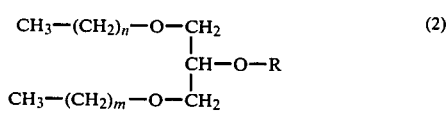

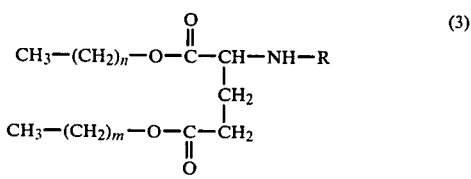

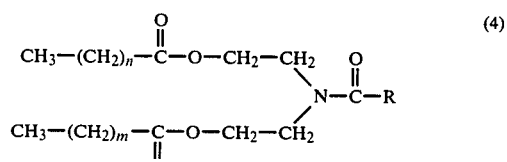

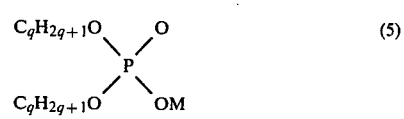

wherein n and m independently represent an integer of 9 through 19, R is a member selected from the following groups:

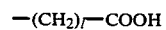

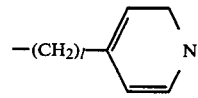

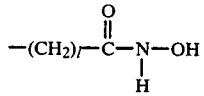

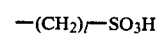

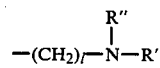

(l is an integer of 1 through 5, and R' and R" independently represent H or CH$_3$), q is an integer of 7 through 20, and M represents a metallic atom.

* * * * *